US006997989B2

(12) United States Patent
Spencer et al.

(10) Patent No.: US 6,997,989 B2
(45) Date of Patent: Feb. 14, 2006

(54) MEDICAL IMPLANT PROCESSING CHAMBER

(75) Inventors: Steven Spencer, Minneapolis, MN (US); Leo Klisch, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/728,751

(22) Filed: Dec. 8, 2003

(65) Prior Publication Data

US 2005/0120951 A1    Jun. 9, 2005

(51) Int. Cl.
    *B05B 13/02*     (2006.01)
(52) U.S. Cl. ...................... 118/321; 118/313; 118/323
(58) Field of Classification Search ............... 118/303, 118/410, 411, 405, DIG. 5, DIG. 7, 718, 118/716, 728, 719, 52, 323, 309, 320, 321, 118/326, 313–316; 34/611–630
    See application file for complete search history.

(56) References Cited

U.S. PATENT DOCUMENTS

| 3,251,337 A | * | 5/1966 | Latta et al. ................. 118/716 |
| 3,682,185 A | * | 8/1972 | Murray et al. .......... 134/122 R |
| 4,593,168 A | * | 6/1986 | Amada ........................ 219/753 |
| 5,328,720 A | * | 7/1994 | Emken et al. ............... 427/213 |
| 5,352,261 A | * | 10/1994 | Aikawa et al. ................ 65/530 |
| 5,464,650 A | * | 11/1995 | Berg et al. .................... 427/2.3 |
| 6,183,565 B1 | * | 2/2001 | Granneman et al. ........ 118/725 |
| 6,368,658 B1 | * | 4/2002 | Schwarz et al. ............ 427/2.15 |
| 6,569,292 B1 | * | 5/2003 | Coffer ......................... 204/164 |
| 6,824,619 B1 | * | 11/2004 | Kuznetsov et al. ......... 118/730 |
| 2002/0012741 A1 | | 1/2002 | Heinz | |
| 2002/0127327 A1 | | 9/2002 | Schwarz et al. | |

* cited by examiner

*Primary Examiner*—Brenda Adel Lamb
(74) *Attorney, Agent, or Firm*—Kenyon & Kenyon

(57) ABSTRACT

Apparatus and method for treating medical implants are provided. The apparatus may include a vessel having a treatment chamber with an inside surface, an outside surface, an entrance, a plurality of fluid passages passing from the outside surface to the inside surface, and a compressible fluid supply line coupled to at least one of the fluid passages. In this embodiment, passages may be positioned and sized to create a buffer zone of compressible fluids between the inside surface of the treatment chamber and a medical implant placed therein. The method may include placing a first medical implant into a treatment chamber having inside surfaces, retarding the first medical implant from contacting the inside surfaces of the treatment chamber by injecting compressible fluid into the treatment chamber, injecting a therapeutic into the treatment chamber, and removing the first medical implant.

16 Claims, 3 Drawing Sheets

MEDICAL IMPLANT PROCESSING CHAMBER

FIELD OF THE INVENTION

The present invention is directed to a chamber or vessel for interfacing medical implants with therapeutic, coatings or both. More specifically, the present invention is directed to a chamber or vessel that uses a cushion of compressible fluid to levitate one or more medical implants to be treated.

BACKGROUND

The positioning and deployment of therapeutic laden implants at a target site inside the body of a patient is an often repeated medical procedure. The benefits and purposes of delivering and placing implants and therapeutics at a target site in the body of a patient are innumerable and can include enlarging constricted lumens, reinforcing recently re-enlarged lumens, replacing ruptured vessels, and treating designated regions, systems, and areas with therapeutic.

The vessels, lumens, and other target sites, which can be treated by implants alone or implants combined with therapeutics, may be located throughout the body and can include the coronary vasculature, the esophagus, the trachea, the colon, the biliary tract, the urinary tract, the prostate, the brain, and the various other organs. Examples of implants that have been used in these or other applications include vena cava filters, stents, stent-grafts, vascular grafts, and intraluminal paving systems.

Implants used in these and other procedures may have the therapeutic positioned on their outside surface, their inside surface, and imbedded or otherwise carried by or within the material that comprises the implants. Moreover, these implants may also have been coated with a polymer or other material. The present invention is directed to new and inventive methods, systems, and apparatus for coating or otherwise interfacing medical implants, such as expandable stents, with therapeutics, coatings or both.

BRIEF DESCRIPTION

A medical implant processing chamber and systems and methods of processing a medical implant are provided in the various embodiments of the present invention. These embodiments include a vessel having a treatment chamber with an inside surface, an outside surface, an entrance, a plurality of fluid passages passing from the outside surface to the inside surface, and a compressible fluid supply line coupled to at least one of the fluid passages. In this embodiment, the passages may be positioned and sized to create a buffer zone of compressible fluids between the inside surface of the treatment chamber and a medical implant placed therein. Embodiments of the present invention also include placing a medical implant into a treatment chamber, obstructing the medical implant from contacting the inside surfaces of the treatment chamber by injecting compressible fluid into the treatment chamber, injecting a therapeutic into the treatment chamber, and removing the medical implant.

DETAILED DESCRIPTION

Figure 1:
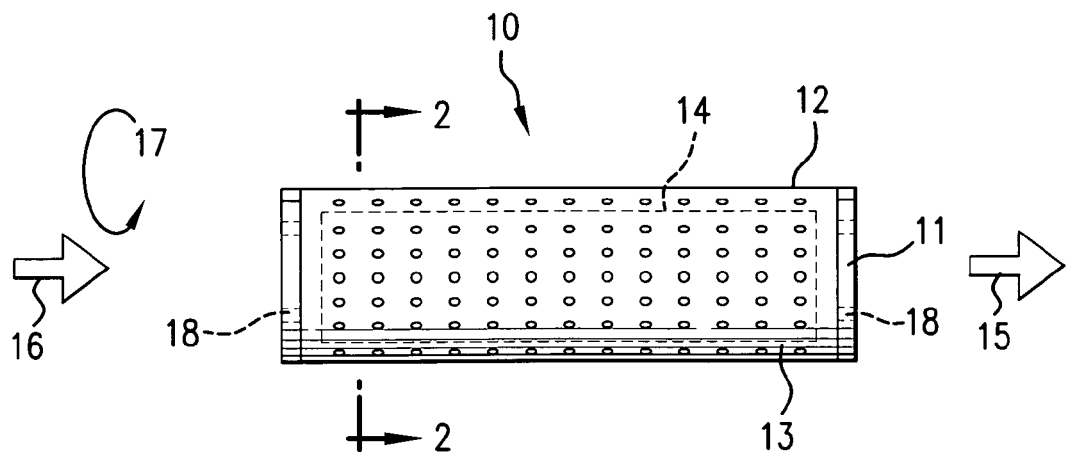
FIG. 1 is a side view of a treatment chamber in accord with an embodiment of the present invention.

FIG. 1 is a side view of a treatment chamber 10 in accord with an embodiment of the present invention. In this embodiment, the treatment chamber 10 includes an outer wall 12 and end plates 11. The outer wall 12 may include a plurality of fluid passages 13 that may be designed and sized to allow compressible fluids, such as air, nitrogen, carbon dioxide, and other compressible gases, to pass from outside the outer wall 12 to inside the outer wall 12 and, consequently, into the chamber 10. The end plates 11 in this embodiment may include exhausts 18, which may be sized and designed to allow compressible fluid entering the treatment chamber 10 to be exhausted from the chamber 10. The end plates 11 may be rotatably coupled to the chamber wall 12 such that they may swing away from the chamber 10 to allow an implant 14 to be placed within the chamber 10 for treatment. Arrow 17 indicates the rotational movement of the end plates 11.

As indicated above, when end plate 11 is in an open position an implant 14 may be placed in the treatment chamber 10 in the direction of arrow 16. Once the implant 14 has been placed within the chamber, it may then be treated, coated or otherwise interfaced with a therapeutic or other material. Once the implant 14 has been interfaced with the therapeutic or other material, it may exit the treatment chamber 10, in the direction of arrow 15, after the end plate 11 has been swung away and opened. Once the implant has been treated and removed, another implant may be placed in the chamber for its own treatment. This treatment cycle may be repeated as necessary. Alternatively, the treatment chamber 10 may be designed or constructed to be used only a single time and then discarded.

Before, during, and after the implant is positioned within the treatment chamber 10, compressible fluid may be injected into the treatment chamber 10 to retard or preclude the implant 14 from contacting the inner walls of the treatment chamber 10. The levitation that results from this injection of compressible fluid may be helpful to prevent therapeutic or other material, which coats or has otherwise been deposited in or on the implant, from being unwantedly damaged, removed or compromised while the implant 14 is in the treatment chamber 10. As described in greater detail below, the implant 14 may be suspended by the injection of air or some other suitable compressible fluid into the treatment chamber 10. The injection of the compressible fluid into the chamber 10 creates a buffer zone or fluid bearing between the implant 14 and the walls 11 of the treatment chamber 10.

While the implant 14 is within the treatment chamber 10, therapeutic may be injected into the treatment chamber 10 to coat or otherwise treat the implant. This therapeutic may be preferably injected while the implant is being suspended, levitated or rotated by the compressible fluid. The buffer zone 22 created by the compressible fluids injected into the treatment chamber serves to retard or prevent unwanted contact between the implant and the treatment chamber 10. This unwanted contact could remove, damage or otherwise compromise therapeutic that coats or is carried by the implant 14. Thus, by suspending or levitating the implant away from the treatment chamber 10 walls, an implant may be treated or coated with a therapeutic within the chamber 10 and then removed from the chamber without the treated implant coming in contact with or being significantly compromised by errant contact with the inner walls of the treatment chamber 10. In addition, to further prevent the therapeutic from being compromised, it may be allowed to dry on the implant 14 while the implant 14 remains within the treatment chamber 10.

Therapeutic may be injected through the same fluid passages 13 that are injecting the compressible fluid into the treatment chamber. Therapeutic may also be injected into fluid passages that do not contain or are not carrying compressible fluid used to levitate the implant within the treatment chamber 10. Thus, in this and other embodiments, the fluid passages may be carrying therapeutic, compressible fluids coatings or a combination. Where both therapeutic, coatings or both and compressible fluids are being carried through the same fluid passage the therapeutic or coatings may be mixed with the compressible fluid upstream of the fluid passage 13 or may be atomized at or near the entrance or exit of the fluid passage 13.

Figure 2:
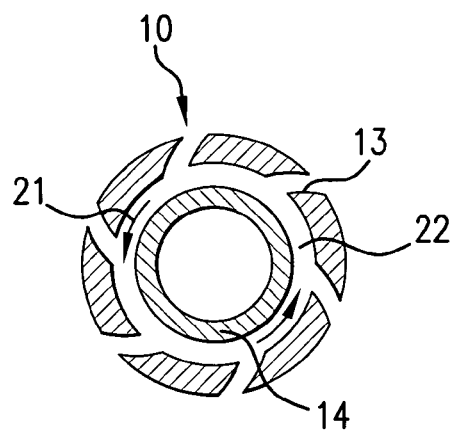
FIG. 2 is a sectional view taken along line 2—2 of FIG. 1.

The fluid passages 13 in this and other embodiments may be angled to circulate the compressible fluid in a vortex or other defined fluid pattern within the treatment chamber 10. FIG. 2, which is a sectional view taken along line 2—2 of FIG. 1, shows how the fluid passages 13 may be angled to create a counterclockwise rotation of compressible fluids within the treatment chamber 10. Arrows 21 indicate the direction of rotation of the fluid and the implant 14 within the treatment chamber 10. Numeral 22 shows the buffer zone created between the implant 14 and the inner walls of the treatment chamber 10.

Treatment chamber as used herein may be any vessel having defined walls with inside surfaces. A treatment chamber may be made from various materials including clear, translucent, and opaque polymers, metals, and ceramics. Clear polymers, which provide for the internal viewing of implants being coated or impregnated with therapeutics in the treatment chamber, may be used in a preferred embodiment. The treatment chamber may be preferably cylindrical but it may be other shapes as well. These shapes may include octagons, other multi-sided polygons, ovals, and non-symmetrical shapes. Furthermore, the treatment chamber may be sized to hold one or more implants.

In a preferred embodiment, a treatment chamber may be sized to allow implants to be positioned end to end next to one another but not side by side. In other words, in a preferred embodiment where both the implants and the treatment chamber are cylindrical, the inside diameter of the treatment chamber may be slightly larger than the outside diameter of the implant to be coated. For instance if the outside diameter of a stent to be coated was 0.5 mm, the inside diameter of the treatment chamber may be 0.7 mm.

While cylindrical implants have been shown, any implant that may be levitated within the treatment chamber and subsequently treated may be used. It is preferred that any implant to be coated should be easily rotatable about at least one of its axes. In other words, it is preferred that an implant to be treated be able to be readily and consistently spun about one of its axes. Consistent rotation about at least one axis can reduce the likelihood that a rotating, suspended implant will contact an inside surface of a treatment chamber before, during, and after it is interfaced with coating or other treatment. Thus, by reducing the likelihood of unwanted contact, the risk of chipping the coating or removing therapeutic from the implant is reduced.

The flow rate and pressure of the compressible fluid injected into the treatment chamber 10 and the size and placement of the fluid passages 13 may be adjusted to accommodate the size, shape, and weight of the implant to be coated. It may also be adjusted depending upon the compressible fluid being used and the pressure developed within the coating chamber. The size and placement of the exhaust ports 18 may also affect the flow rate and pressure of the compressible fluid being used. Still further, to adjust the amount of compressible fluid that may be needed to levitate an implant, the implants may be loaded into the chamber in various orientations, i.e., forward, backward, open, and closed (in the case of an expandable implant).

Figure 3:
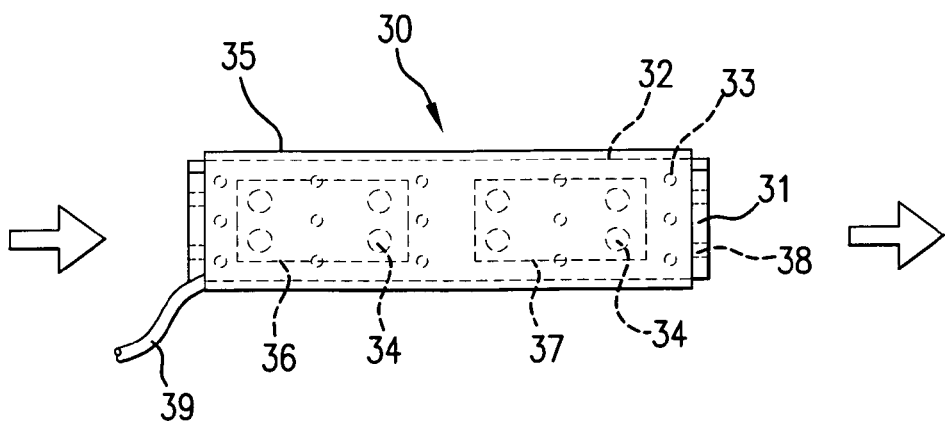
FIG. 3 is a side view of a treatment chamber in accord with another embodiment of the present invention.

FIG. 3 is a side view of an alternative treatment chamber 30 in accord with another embodiment of the present invention. In FIG. 3, an outer case 35 has been placed around the treatment chamber 32. This outer case 35 has a supply line 39 that may be used to supply compressible fluids, therapeutics and coatings to the outer case 35. As the outer case 35 surrounds and tightly engages the treatment chamber 32, compressible fluids, therapeutics and coatings entering the outer case 35 through the supply line 39 may be ultimately forced through the fluid passages 33 and 34 to the inside of the treatment chamber 32. The compressible fluids entering the treatment chamber 32 may form a buffer zone with any implant placed therein while the therapeutic may coat or otherwise interface with an implant in the treatment chamber 32.

In this embodiment, the fluid passages in the treatment chamber are shown having two different diameters, a larger diameter 34 and a smaller diameter 33. By changing the diameters, shapes and sizes of the fluid passages different fluid circulation patterns may be created within the treatment chamber. It may be beneficial to create varying circulation patterns within the treatment chamber in order to accommodate a specific shape or design of an implant to be coated. In other words, depending upon the design of the implant, it may be necessary to provide more levitational force at certain points of the implant than at others. This may be required due to uneven weighting of the implant or varying surface designs of the implant. By varying the sizes and spacing of the fluid passages, the requisite varying lifting forces can be provided.

As can be seen in FIG. 3, the treatment chamber 32 and outer case 35 are sized to accommodate two implants, a first implant 36 and a second implant 37. These implants have been placed end to end in this figure. As can also be seen, the treatment chamber, like the one on FIG. 1, has two end plates 31, one at each end. Like FIG. 1, these end plates swing up and away to allow access to the treatment chamber and seal tight against the treatment chamber when they are closed during the coating and levitation processes. While circular end plates that swing on an end are shown, various other configuration may also be plausible. Also, while the exhaust passages 38 are shown on the end plate 31, they may be placed at other locations of the treatment chamber 32 as well.

Figure 4:
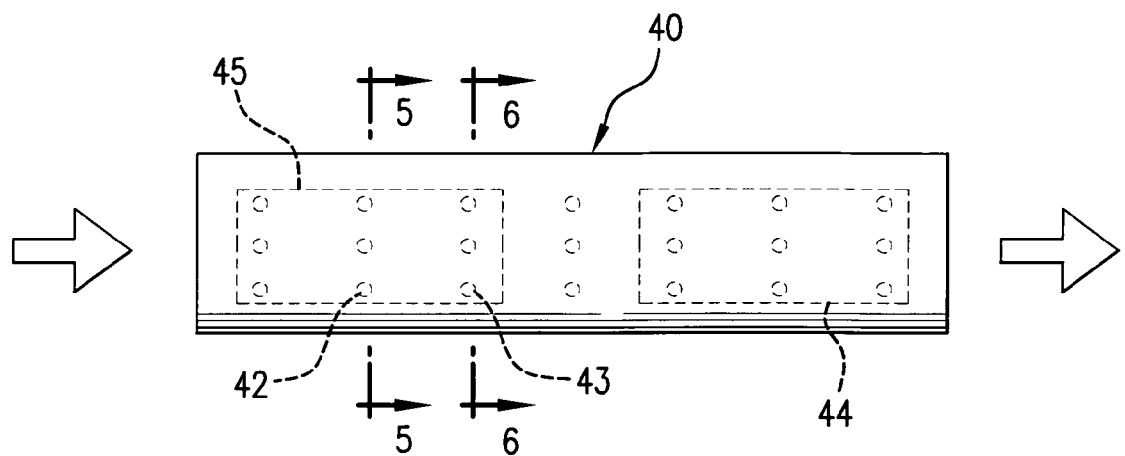
FIG. 4 is side view of a treatment chamber in accord with another embodiment of the present invention.

FIG. 4 is a side view of another embodiment of the present invention. In FIG. 4, the treatment chamber 40 contains clockwise fluid passages 42 and counter clockwise fluid passages 43 as well as a first implant 45 and a second implant 44. Arrows 46 indicate the direction of travel of the implants 45 and 44 through the treatment chamber 40. In this embodiment, the implants may be fed through the treatment chamber in multiple batches or in a continuous feed process. As can be seen, the treatment chamber 40 is sized to contain two implants at the same time.

Still further, the fluid passages in this embodiment may be fed by independent sources of compressed fluid. Thus, depending upon which fluid passages are being fed compressed fluid, the implants may be rotated clockwise or counter-clockwise within the treatment chamber. This may be done to facilitate uniform application or drying of therapeutic or coatings onto the implants. The therapeutic in this embodiment as well as in the others may be added to the treatment chamber via the fluid passages or may be introduced into the treatment chamber with other means. For instance, as described in greater detail below, a nozzle may be placed inside the treatment chamber and the implant and therapeutic may be injected or sprayed into the treatment chamber via this nozzle. In so doing, the force of the rotating implant may be used to draw the therapeutic from the inside of the implant to the outside of the implant. This may be useful when both the inside and outside surfaces of the therapeutic needs to be covered. It may also be useful when the therapeutic is carried within the implant and needs to be migrated towards the outer surface of the spinning implant. In other words, when therapeutic or some coating material is injected on the inside of the implant, the outward forces associated with the rotation of the implant may cause the therapeutic to migrate through the implant or along its surfaces from the inside to the outside if the implant as it is levitated and spun.

Still further, different therapeutics may be fed into the chamber at different locations along the chamber in this and other embodiments. In so doing, the individual implants may be coated with different therapeutics at different locations on the implant. Likewise, the implants may also be coated in layers of different therapeutics, with the upstream therapeutic creating the underlayer of a first therapeutic and the downstream therapeutic creating the upper layer of a second therapeutic.

Figure 5:
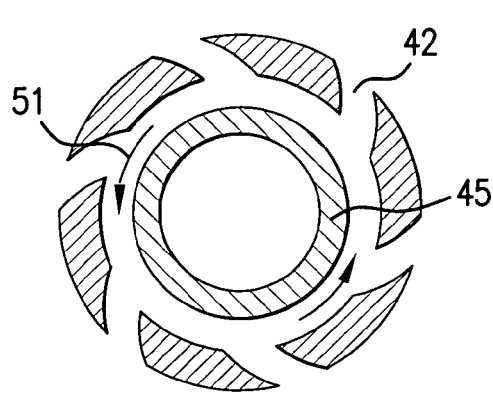
FIG. 5 is a sectional view taken along line 5—5 of FIG. 4.

FIG. 5 is a sectional view taken along line 5—5 of FIG. 4. The sectional view of the implant 45, the treatment chamber 40, and the clockwise fluid passages 42 can be seen in this view. Arrows 51 indicate the direct of the fluid flow within the treatment chamber as well as the rotations direction of the implant 45. While the clockwise fluid passages 42 are shown with uniform cross-sections, they may also have non-uniform cross-sections such as conical or ridged cross sections, which would accelerate fluid flowing through these passages.

Figure 6:
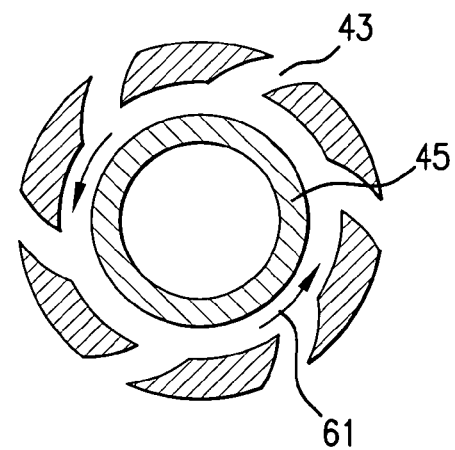
FIG. 6 is a sectional view taken along line 6—6 of FIG. 4.

FIG. 6 is a sectional view taken along line 6—6 of FIG. 4. The sectional view of the implant 45, the treatment chamber 40, and the counterclockwise fluid passages 43 can be seen in this view. Arrows 61 indicate the direct of the fluid flow within the treatment chamber as well as the rotational direction of the implant 45. As above, while the counter-clockwise fluid passages 43 are shown with uniform cross-sections, they may also have non-uniform cross-sections such as conical or ridged cross-sections, which would accelerate fluid flowing through these passages.

Figure 7:
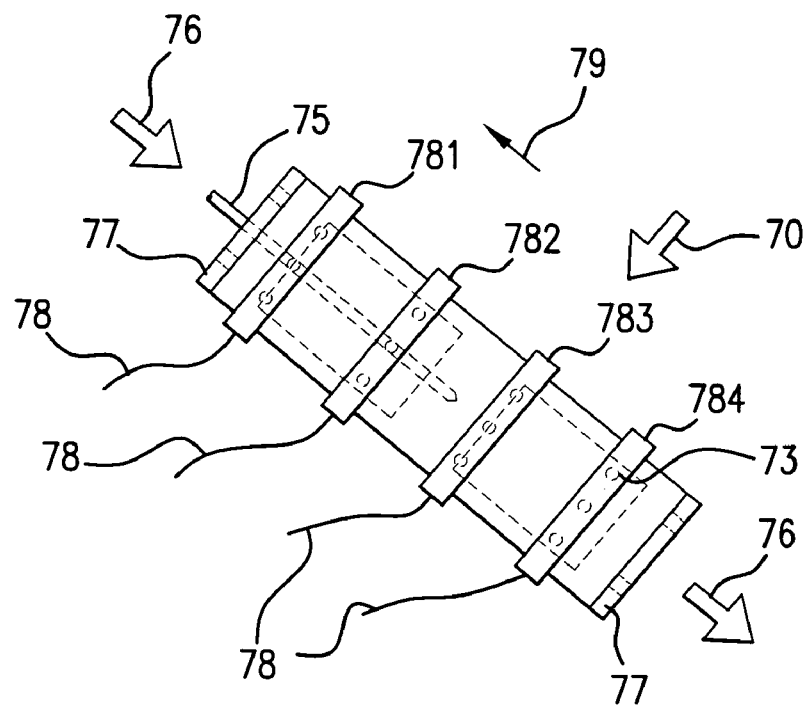
FIG. 7 is a side view of a treatment chamber in accord with another embodiment of the present invention.
Figure 8:
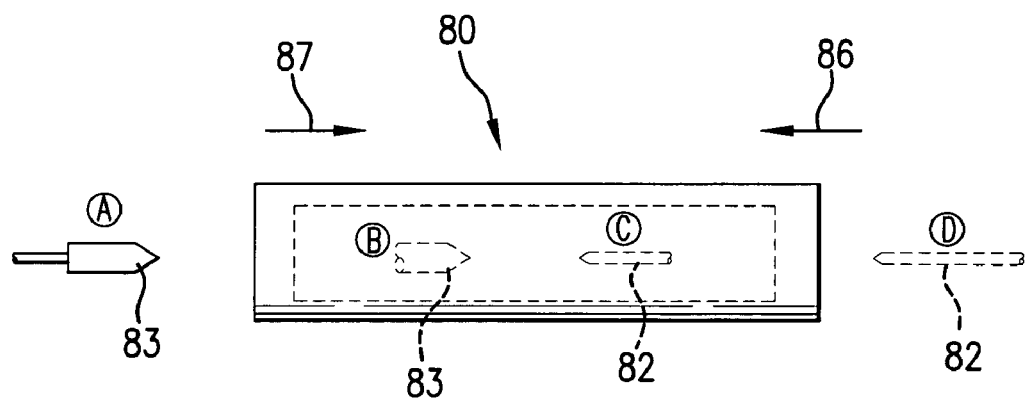
FIG. 8 is a side view of a treatment chamber in accord with another embodiment of the present invention.

FIG. 7 is a side view of another alternative embodiment of the present invention. In this embodiment, the treatment chamber 70 is maintained on an angle with its entrance being higher than its exit. The direction of flow of implants being processed in the treatment chamber 70 can be seen with arrows 76. The treatment chamber 70 contains end plates 77 and has several fluid lines 78 coupled to it. These fluid lines 78, which are coupled to fluid passages in the treatment chamber 70, may be individually controlled to control the rotation, drying, movement, etc. of the implants begin treated within the treatment chamber. Thus, in a batch process application, an implant may be fed in the entrance of the treatment chamber and suspended by the air leaving fluid lines 781 and 782, while air leaving fluid line 783 prevents the implant from advancing further down into the treatment chamber. The air passing through 783 into the treatment chamber may then be reduced, allowing the implant to pass. In the next portion of the treatment chamber, a second therapeutic may be added, a second layer may be added, and the therapeutic may be dried. Upstream of the implant, after it has moved, a second implant may also be added to be treated as well. This implant may be retained in the uphill portion of the treatment chamber by increasing fluid flow though line 783. Alternatively, the lines may be sequentially activated to both suspend and urge the implant through the coating chamber. In this example, the downstream lines may be only activated once the implant is moved near and, in so doing, the implant may be urged through the treatment chamber.

As suggested above, therapeutic may be injected into the treatment chamber by a therapeutic nozzle. This nozzle 75 may move inside the rotating implant and eject therapeutic from its tip while it is being drawn back, out of the chamber, in the direction of arrow 79.

The treatment chamber in this embodiment and other embodiments may also contain drying coils that may be activated to heat and dry the therapeutic onto the implant prior to the implants removal from the chamber.

FIG. 9 is a side view of another embodiment of the present invention. In this embodiment the treatment chamber 80 has two therapeutic nozzles 82 and 83, one for each end. Therapeutic nozzle 83 may move from position b to position a as an implant is treated while therapeutic nozzle 82 may move from position c to position d as an implant is treated. As can also be seen, the therapeutic nozzles may have various configurations. These configurations may depend upon the therapeutic being ejected.

Medical implants that may be coated or treated in accord with the present invention include catheters, vascular catheters, balloon catheters, guide wires, balloons, filters (e.g., vena cava filters), vascular stents (including covered stents such as PTFE polytetrafluoroethylene)-covered stents), stent grafts, cerebral stents, cerebral aneurysm filler coils (including GDC (Guglielmi detachable coils) and metal coils), vascular grafts, myocardial plugs, pacemaker leads, heart valves and intraluminal paving systems, filterwires, venous valves, bifurcation stents, and aortic stents.

Therapeutics that may be used are numerous and include pharmaceutically active compounds, nucleic acids with and without carrier vectors such as lipids, compacting agents (such as histones), viruses (such as adenovirus, adenoassociated virus, retrovirus, lentivirus and a-virus), polymers, hyaluronic acid, proteins, cells and the like, with or without targeting sequences.

Other examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application.

Non-limiting examples of virus vectors or vectors derived from viral sources include adenoviral vectors, herpes simplex vectors, papilloma vectors, adeno-associated vectors, retroviral vectors, and the like.

Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomnine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site.

Polynucleotide sequences useful in practice of the invention include DNA or RNA sequences having a therapeutic effect after being taken up by a cell. Examples of therapeutic polynucleotides include anti-sense DNA and RNA; DNA coding for an and-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor " and $, platelet-derived endothelial growth factor, platelet-derived growth factor, tumor necrosis factor ", hepatocyte growth factor and insulin like growth factor, growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMIP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Coatings used with the present invention may comprise various polymeric material/drug agent matrices. These may be formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The carriers and coatings used in the present invention may be hydrophilic or hydrophobic and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

While various embodiments of the present invention have been described, other embodiments are also plausible. For instance the multiple fluid lines of FIG. 7 may be used on the embodiment of FIG. 3 in order to allow selective activation of the various small and large fluid passages. Likewise, while passages are generally shown as being consistently sized along the same circumference of the treatment chamber that may not always be the case as the passages may be different sizes or shapes along the same circumferential line. Moreover, the passages may not always be along uniform cross-sectional lines.

What is claimed is:

1. A system for treating medical implants comprising:
    a treatment chamber having
        an inside surface defining the inside of the treatment chamber,
        an outside surface,
        an entrance sized to allow a medical implant to pass through it,
        a plurality of fluid passages,
    a compressible fluid supply in fluid communication with at least one of the fluid passages, and
    an elongated medical implant having a longitudinal axis,
    wherein the plurality of fluid passages are positioned and sized to create a buffer zone of compressible fluid between the inside surface of the treatment chamber and the medical implant positioned at least partially within the chamber when compressible fluid has exited the passages and
    wherein the plurality of fluid passages are positioned and sized such that when compressible fluid has exited the passages, the elongated medical implant positioned at least partially in the treatment chamber will spin about its longitudinal axis.

2. The system for treating medical implants of claim 1 further comprising:
    a therapeutic injection nozzle positioned within the treatment chamber along a longitudinal axis of the treatment chamber.

3. The system for treating medical implants of claim 1 wherein the treatment chamber is cylindrical and the plurality of fluid passages are uniformly spaced and positioned along the inside surface of the treatment chamber.

4. The system for treating medical implants of claim 1 further comprising:
    an outer case surrounding the treatment chamber;
    a coating supply coupled to the treatment chamber; and
    a heating element in thermal communication with the inside surface of the treatment chamber.

5. The system for treating medical implants of claim 1 wherein the fluid passages are coupled to a supply of coating and therapeutic.

6. The system for treating medical implants of claim 1 wherein the treatment chamber is cylindrically shaped and further comprises:
    an end cap; and
    an exhaust,
        wherein the plurality of fluid passages positioned and sized to circulate compressible fluid within the treatment chamber, and the treatment chamber is sized to treat a single medical implant at a time.

7. The system for treating medical implants of claim 1 wherein a coating source, a therapeutic source, and a compressible fluid source are each coupled to the fluid passages.

8. The system for treating medical implants of claim 1 further comprising:
    a first nozzle positioned within the treatment chamber, the first nozzle slidable along a longitudinal axis of the treatment chamber, the first nozzle coupled to a supply of therapeutic or coating; and
    a second nozzle positioned within the treatment chamber, the second nozzle slidable along a longitudinal axis of the treatment chamber, the second nozzle coupled to a supply of therapeutic or coating.

9. The system for treating medical implants of claim 1 wherein a first set of fluid passages direct circulation of compressible fluids within the treatment chamber in a first direction and wherein a second set of fluid passages direct circulation of compressible fluids within the treatment chamber in a second direction, the first direction different from the second direction.

10. The system for treating medical implants of claim 9 wherein the first direction is opposed to the second direction.

11. The system for treating medical implants of claim 1 wherein the treatment chamber is not opaque.

12. The system for treating medical implants of claim 1 wherein the fluid passages comprise at least a first set of passages and a second set of passages, and wherein compressible fluid may be ejected from the first set of passages regardless of whether compressible fluid is being ejected from the second set of passages.

13. The system vessel for treating medical implants of claim 1 further comprising:
    a supply of a first coating coupled to the treatment chamber; and
    a supply of a second coating coupled to the treatment chamber.

14. The system for treating medical implants of claim 1 wherein the medical implant is a stent.

15. The system for treating medical implants of claim 1 wherein the buffer zone of compressible fluid encircles the medical implant.

16. The system for treating medical implants of claim 1 wherein the buffer zone of compressible fluid prevents contact between the medical implant and the inside surface of the treatment chamber.

* * * * *